United States Patent
Drechsler (10) Patent No.: US 9,237,991 B2
(45) Date of Patent: *Jan. 19, 2016

(54) DENTAL RESTORATIVE MATERIAL

(71) Applicant: Kerr Corporation, Orange, CA (US)

(72) Inventor: Ulf Drechsler, Claremont, CA (US)

(73) Assignee: Kerr Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/474,598

(22) Filed: Sep. 2, 2014

(65) Prior Publication Data

US 2014/0371342 A1    Dec. 18, 2014

Related U.S. Application Data

(63) Continuation of application No. 13/478,396, filed on May 23, 2012, now Pat. No. 8,822,564.

(60) Provisional application No. 61/491,089, filed on May 27, 2011.

(51) Int. Cl.
| | |
|---|---|
| *A61K 6/087* | (2006.01) |
| *C08L 63/00* | (2006.01) |
| *A61K 6/08* | (2006.01) |
| *A61K 6/083* | (2006.01) |
| *A61K 6/00* | (2006.01) |
| *A61K 6/027* | (2006.01) |

(52) U.S. Cl.
CPC ............... *A61K 6/087* (2013.01); *A61K 6/005* (2013.01); *A61K 6/0008* (2013.01); *A61K 6/0088* (2013.01); *A61K 6/027* (2013.01)

(58) Field of Classification Search
None
See application file for complete search history.

(56) References Cited

U.S. PATENT DOCUMENTS

| | | | | |
|---|---|---|---|---|
| 4,857,111 | A | * | 8/1989 | Haubennestel et al. ...... 106/504 |
| 5,116,885 | A | | 5/1992 | Hattori et al. |
| 5,244,933 | A | | 9/1993 | Eidenbenz et al. |
| 5,536,871 | A | * | 7/1996 | Santhanam .................... 560/196 |
| 6,010,085 | A | * | 1/2000 | Angeletakis ..................... 241/21 |
| 6,098,906 | A | | 8/2000 | Angeletakis |
| 6,121,344 | A | * | 9/2000 | Angeletakis et al. ......... 523/116 |
| 6,127,450 | A | * | 10/2000 | Angeletakis .................. 523/116 |
| 6,232,367 | B1 | | 5/2001 | Kobashigawa et al. |

(Continued)

OTHER PUBLICATIONS

Chinese Patent Office, First Office Action issued in corresponding Chinese Application No. 201210243102.7 dated Jan 22, 2015, 9 pp., including English translation, 8 pp.

(Continued)

*Primary Examiner* — Peter A Salamon
(74) *Attorney, Agent, or Firm* — Wood, Herron & Evans, LLP (57) ABSTRACT

A dental restorative composition is provided that includes a polymerizable resin, a substantially translucent structural filler, a nanofiller having a mean particle size less than 100 nm, and at least one rheology-modifying additive. In one embodiment, the structural filler has a refractive index substantially similar to that of the polymerizable resin, a coarse particle fraction, and a fine particle fraction having a mean particle size greater than 0.1 μm and smaller than the mean particle size of the coarse particle fraction. The relative ratio of the coarse particle fraction to the fine particle fraction is in the range from about 12:1 to about 2:1 by volume, the particle size distribution of each fraction is essentially monomodal, and the D(90) of the fine particle fraction is less than or equal to the D(10) of the coarse particle fraction.

19 Claims, 2 Drawing Sheets

(56) References Cited

U.S. PATENT DOCUMENTS

| | | | | |
|---|---|---|---|---|
| 6,300,390 B1 * | 10/2001 | Angeletakis | ............... | 523/116 |
| 6,395,803 B1 * | 5/2002 | Angeletakis | ............... | 523/116 |
| 6,890,968 B2 * | 5/2005 | Angeletakis et al. | ......... | 523/115 |
| 7,014,462 B1 | 3/2006 | Tilse | | |
| 2002/0128347 A1 | 9/2002 | Blackwell et al. | | |

OTHER PUBLICATIONS

European Patent Office, European Search Report and Search Opinion issued in corresponding European Application No. 12169365.9 dated Oct 7, 2014, 10 pp.

* cited by examiner

DENTAL RESTORATIVE MATERIAL

CROSS-REFERENCE TO RELATED APPLICATION

This application is a continuation of U.S. Pat. No. 8,822,564, issued Sep. 2, 2014 and entitled DENTAL RESTORATIVE MATERIAL, which claims the benefit of and priority to prior filed Provisional Application Ser. No. 61/491,089, filed May 27, 2011, the disclosures of which are incorporated herein by reference in their entirety as if completely set forth herein below.

FIELD OF THE INVENTION

The present invention relates to resin based materials for use in restorative dentistry. More specifically, the invention relates to resin composite materials suitable for simplified placement by the dental practitioner, which materials exhibit paste-like viscosity in an undisturbed state and a liquid-like flowable viscosity when subjected to vibration energy.

BACKGROUND OF THE INVENTION

Posterior and anterior tooth restoration is typically achieved by excavating decayed tooth structure and filling the resulting cavity with a paste-like filling material, which is then hardened by chemical or photochemical curing processes. Resin based dental restorative materials are becoming the material of choice by dentists and patients due to desirable esthetic properties. Tooth colored resin based composite materials are usually composed of dispersions of inorganic filler particles in a polymerizable organic resin matrix. Most commonly, especially in direct restorations, the restorative material is cured by exposure to actinic radiation.

Stress bearing restorations, such as those involving the occlusal surface of posterior teeth, require the use of mechanically strong, highly filled restorative materials to withstand the forces resulting from mastication. Such restorative materials are typically highly viscous, which makes accurate placement of the restorative difficult and highly technique sensitive. Inadvertently, the cavity may be insufficiently filled and adaptation of the restorative material to the cavity walls may be incomplete, resulting in gaps between the restoration and the tooth structure, which can lead to increased sensitivity, intrusion of fluids and bacteria, and can result in continued tooth decay and premature failure of the restoration. Less highly filled, flowable restorative materials, on the other hand, facilitate proper adaptation but lack the required strength for stress bearing restorations. Moreover, since these less highly filled materials tend to flow under their own weight, they cannot be shaped to conform to the original tooth anatomy.

When using highly filled restorative materials to restore a deep cavity, the material is typically placed incrementally in thin layers. Each incremental layer is cured individually before placing the subsequent increment to counteract both polymerization shrinkage stress and low light penetration depth and thus incomplete hardening of the restorative. Restoring a tooth using the layering technique is therefore relatively time consuming and also increases the risk of leaving voids between the layers, which could significantly weaken the restoration.

It is therefore desirable to provide a highly filled, paste-like restorative material having a high viscosity that can be lowered to a liquid-like flowable consistency when dispensed into a cavity by using an external stimulus and that the initial paste-like viscosity is restored upon removal of said external stimulus to facilitate shaping to the proper contour. Furthermore it is desirable for this material to exert low polymerization shrinkage stress to the restored tooth and to exhibit sufficient depth of cure to enable placement and adequate hardening of fewer but thicker layers of the restorative material. Ideally, the entirety of such a restorative material required to fill the whole cavity would be placed and hardened in bulk.

It is known that particulate dispersions with high solids content, of which dental restorative composites are examples, typically exhibit shear-thinning and, in some cases, thixotropic behavior and that their viscosity can be lowered through the action of vibrations, including sonic or ultrasonic vibrations. For example, U.S. Pat. No. 5,244,933 discloses dental compositions having a viscosity too high to be workable for the intended purpose, which can be rendered workable by exposure to oscillations. When used clinically for restoring a tooth defect, however, such otherwise unworkable materials require the use of special oscillating equipment throughout each manipulation step, which makes their use cumbersome and thus presents a disadvantage to the practitioner. Prior art paste-like resin based restorative materials, including universal composite materials such as Herculite® (Kerr Corp., Orange, Calif.) can be dispensed at a reduced viscosity through the use of special vibration-assisted dispensers. For example, U.S. Pat. No. 7,014,462 discloses a method and a device for introducing a dental filling material into a tooth cavity, where the device subjects the filling material to the action of vibrations as is it injected into the cavity. However, the ease and extent of viscosity reduction of a given material through the action of sonic or ultrasonic vibrations varies and is highly dependent on the material's composition. Moreover, since vibration-induced liquefaction is accompanied by heat generation due to internal friction, simply increasing the power or duration of the vibrating action to improve efficiency can lead to a substantial temperature rise, which could potentially harm the tooth. For these practical reasons, the degree of liquefaction of prior art dental restoratives is limited and, particularly for very highly filled materials, is insufficient to achieve the liquid-like behavior of a flowable restorative material.

In summary, there is a need to provide a highly filled dental restorative material that offers high strength for load bearing restorations, low polymerization shrinkage, and high depth of cure, yet readily liquefies to a flowable-like consistency through activation by vibration energy to greatly simplify clinical placement.

SUMMARY OF THE INVENTION

A dental restorative composition is provided, comprising a polymerizable resin, substantially translucent structural filler, a nanofiller having a mean particle size less than 100 nm, and at least one rheology-modifying additive.

In one embodiment, the structural filler has a refractive index substantially similar to that of the polymerizable resin, and comprises a coarse particle fraction having a first mean particle size, and a fine particle fraction having a second mean particle size greater than 0.1 µm and smaller than the first mean particle size of the coarse particle fraction. The relative ratio of the coarse particle fraction to the fine particle fraction is in the range from about 12:1 to about 2:1 by volume, the particle size distributions of each of the coarse and fine particle fractions are essentially monomodal, and the D(90) of the fine particle fraction is less than or equal to the D(10) of the coarse particle fraction.

In additional or alternative embodiments, the second mean particle size is greater than 0.1 µm and less than 1 µm; the at least one rheology-modifying additive is present in an amount of about 0.1 to about 5 wt. %; the at least one rheology-modifying additive includes an inorganic rheology-modifying additive and an organic rheology-modifying additive; the first mean particle size is greater than about 3 µm; the D(10) of the course particle fraction is ≥1 µm; the D(90) of the fine particle fraction is ≤0.9 µm; the ratio of the structural filler to the nanofiller is in the range of about 20:1 to about 10:1 by volume; the viscosity is paste-like in an undisturbed state, and the composition undergoes shear-thinning to reduce the viscosity to liquid-like in a disturbed state in which the composition is subjected to sonic and/or ultrasonic vibration; and/or the Loss Tangent is <1 in an undisturbed state and >1 in a disturbed state in which the composition is subjected to sonic and/or ultrasonic vibration.

DETAILED DESCRIPTION OF THE INVENTION

The present invention provides a dental restorative material that exhibits a paste-like packable viscosity in its undisturbed state that is readily reduced to a liquid-like flowable viscosity when subjected to vibrations, including sonic and/or ultrasonic vibrations, and exhibits one or more of the following properties: high loading, high mechanical strength sufficient to be suitable for load bearing restorations, low polymerization shrinkage, and high depth of cure sufficient to allow the practitioner to place and adequately harden the material in substantially deeper incremental layers. Advantageously, the inventive material can be used to fill the bulk of a large cavity in one single increment, thereby omitting placement and separate hardening of multiple layers of restorative material as required for prior art dental composites.

In accordance with an embodiment of the invention, the restorative material comprises (1) a polymerizable resin; (2) a substantially translucent structural filler having a refractive index substantially similar to that of the polymerizable resin; (3) a nanofiller; (4) one or more rheology-modifying additives; and optionally (5) other additives including polymerization initiators, dispersants, stabilizers, pigments and the like. The structural filler (2) comprises a coarse particle fraction and a fine particle fraction having a mean particle size substantially smaller than the coarse particle fraction, each fraction being essentially monomodal having a distribution such that the D(90) of the small particle fraction is less than or equal to the D(10) of the large particulate fraction, as defined below, and having a relative ratio of coarse particle fraction to fine particle fraction in the range from about 12 to 1 to about 2 to 1 by volume.

The present invention provides a dental restorative resin based composite material having some or all of the following properties: the material in its undisturbed state exhibits a paste-like viscosity, which can be readily lowered without significant increase in temperature to a liquid-like viscosity when subjected to vibrations including sonic and/or ultrasonic vibrations; high mechanical strength suitable for load bearing restorations; high filler loading; low polymerization shrinkage and low polymerization shrinkage stress; and high depth of cure when polymerized using actinic radiation. By paste-like viscosity it is meant that the material does not flow under its own weight and can be easily shaped by the dental practitioner to follow the natural tooth anatomy. By liquid-like viscosity it is meant that the material flows under its own weight, i.e., is a flowable dental composite as that term is understood in the art, such that it intimately conforms to the contours of the surface to which it is applied without leaving voids between the material and the contacting surface. The inventive material can be used by a dental practitioner to restore a tooth cavity using a greatly simplified clinical procedure involving significantly fewer manipulating steps.

The inventive material comprises a curable resin, preferably a polymerizable resin containing methacrylate monomers. Curing of the composite may be achieved by mixing two paste components containing a catalyst and accelerator, respectively, or by a photopolymerization process wherein the resins are cured when exposed to actinic radiation, such as blue visible light. Photopolymerizable resins containing monomers other than methacrylates may be used in the present invention, as may be appreciated by those skilled in the art, such as cationically photocurable oxiranes, for example.

To provide the inventive material exhibiting the desired rheology, in particular to achieve a pronounced reduction in viscosity upon being subjected to vibrations, the material advantageously exhibits a high degree of shear thinning. Without being bound by theory, the extent of shear thinning can be maximized by employing an essentially uniformly sized structural filler. As can be appreciated by a person skilled in the art, such a material exhibits less desirable handling properties including a tendency to flow under its own weight, which would make shaping by the practitioner very difficult. Furthermore, by using a uniformly sized filler, the desired high degree of loading cannot be achieved, since a high, unfilled interstitial volume between the filler particles remains.

It has now been found that addition of at least one rheology modifying additive to a composition comprising a polymerizable resin and a coarse structural filler having an essentially monomodal particle size distribution significantly improves handling properties, such that a paste-like viscosity is achieved and the material maintains its shape without flowing under its own weight and can thus be easily shaped. Monomodal particle size distribution as used herein refers to a collection of particles whose size distribution curve (particle count as a function of particle size) displays one single maximum and, when particle size is plotted on a logarithmic scale, shows an approximately lognormal distribution. Particle size distribution is measured by known methods, including but not limited to dynamic light scattering methods. Advantageously, addition of at least one rheology modifying additive imparts thixotropic properties to the composite paste, which has been found to improve material flow when being subjected to sonic and/or ultrasonic vibrations.

It has further been found that addition of a fine particle filler, referred to as the fine particle fraction of the structural filler, having an essentially monomodal distribution and having a mean particle size substantially smaller than the coarse particle fraction, such that the D(90) of the fine particle fraction is less than or equal to the D(10) of the coarse particle fraction, greatly increases the degree of loading by filling the interstitial spaces. D(90) is defined as the diameter where

Figure 1:
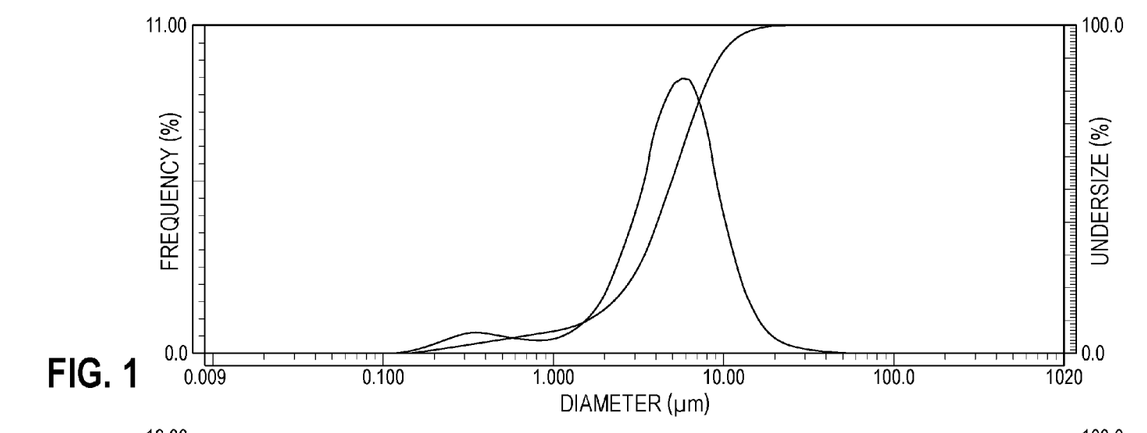
FIG. 1 is a graph of particle size distribution for a coarse particle fraction of a structural filler for use in a composition of the invention.
Figure 2:
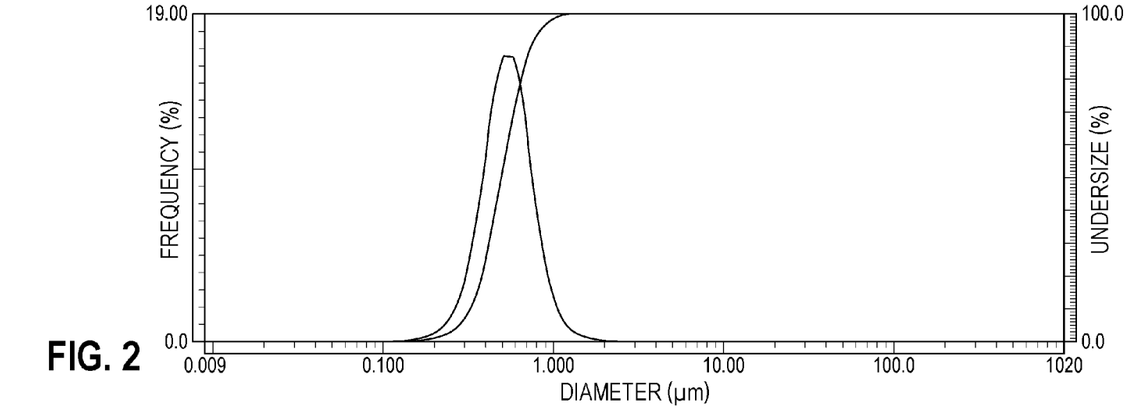
FIG. 2 is a graph of particle size distribution for a fine particle fraction of a structural filler for use in a composition of the invention.
Figure 3:
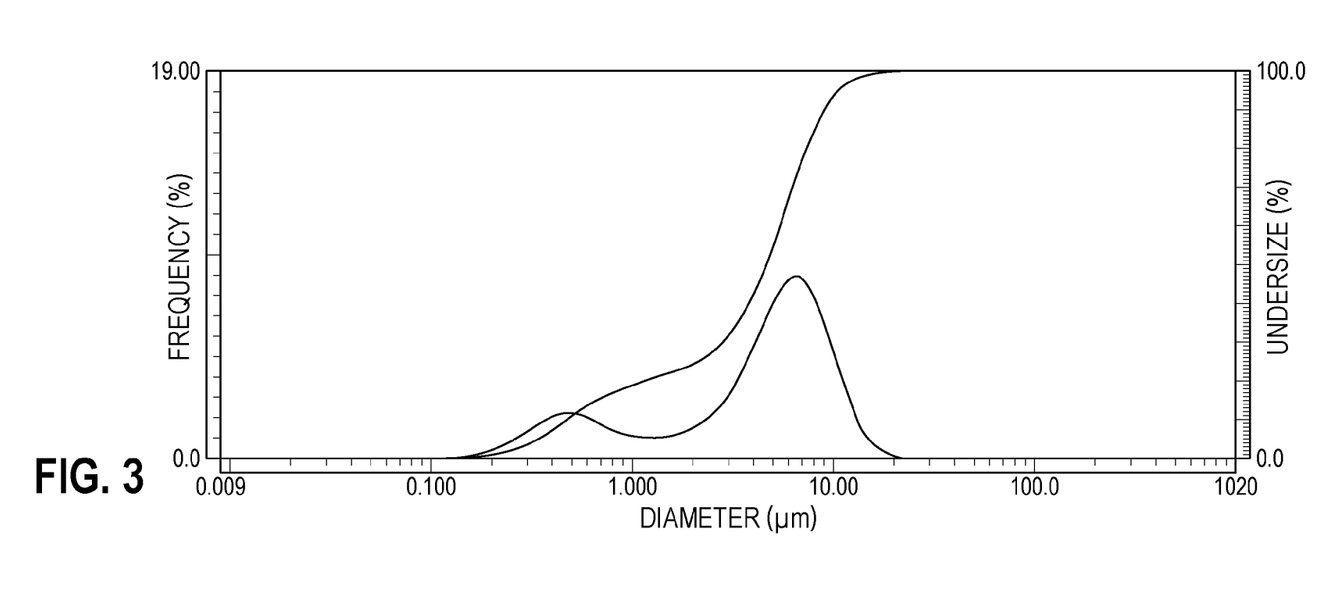
FIG. 3 is a graph of a blended particle size distribution for the structural filler combining the coarse particle fraction of FIG. 1 with the fine particle fraction of FIG. 2.

90% by volume of the particles within the distribution have a smaller diameter. D(10) is defined as the diameter where 10% by volume of the particles within the distribution have a smaller diameter. FIG. 1 graphically depicts a particle distribution of an exemplary coarse particle fraction having a mean particle size of about 5.3 μm, a D10 of about 1.58 μm, and a range of particle sizes of about 0.15-22 μm. FIG. 2 graphically depicts a particle distribution of an exemplary fine particle fraction that may be used with the coarse particle fraction of FIG. 1, the fine particle fraction having a mean particle size of about 0.52 μm, a D90 of about 0.75 μm, and a range of particle sizes of about 0.15-1.5 μm. FIG. 3 graphically depicts the blended particle distribution for the structural filler combining the coarse particle fraction of FIG. 1 with the fine particle fraction of FIG. 2. In another example, a coarse particle fraction having a mean particle size of about 5 μm, a D10 of about 1 μm, a D90 of about 11 and a range of particle sizes of about 0.13-25 μm may be used with the small particle fraction of FIG. 2.

It is advantageous to increase the loading, i.e., the fraction of solids dispersed within the hardenable resin to an extent that upon hardening of the mixture a volumetric shrinkage of less than about 1.8% is achieved. In one embodiment, the fine particle fraction is added at a ratio of coarse to fine particles of about 12 to 1 to about 2 to 1 by volume, since this range still provides the desired high degree of shear thinning. Coarse particle fraction refers to the collection of filler particles falling within the size distribution having the larger mean particle size and does not infer any particular absolute particle size or range. Fine particle fraction refers to the collection of filler particles falling within the size distribution having the smaller mean particle size and does not infer any particular absolute particle size or range; however, for practical reasons, the mean particle size of the fine particle fraction is greater than 0.1 μm. The combined coarse and fine particle fractions are referred to herein as the structural filler.

By way of example only, and not limitation, the coarse particle fraction may have a mean particle size greater than about 3 μm with the size distribution of particles including a D(10) of no less than about 1 μm (i.e., ≥1 μm). Additionally, the fine particle fraction may have a mean particle size greater than about 0.1 μm and less than about 1 μm with the size distribution of particles including a D(90) of no greater than about 0.9 μm. By way of further example, the structural filler may include a coarse particle fraction having a mean particle size in the range of about 4-7 μm with the size distribution of particles including a D(10) of no less than about 1.2 μm and a fine particle fraction having a mean particle size of about 0.3-0.7 μm with the size distribution of particles including a D(90) of no greater than about 0.9 μm.

The structural filler exhibits a particle surface that is sufficiently hydrophobic to increase compatibility with the resin and at the same time minimizes particle-particle interactions. It is particularly useful for the structural filler particles to exhibit a refractive index substantially similar to that of the polymerizable resin, such that RI(filler)−RI(resin)≤about 0.05 and that the filler is substantially translucent. RI(filler) and RI(resin) are the refractive indexes of the filler and the resin, respectively. The translucency of the filler is determined by dispersing 75 parts by weight of filler into 25 parts by weight of hardenable resin where RI(filler)−RI(resin)≤0.05, hardening the paste, and measuring the opacity of the resulting mixture. By having a substantially translucent filler it is meant that a mixture prepared as described is less than 45% opaque. Both properties provide for high depth of cure when the material is hardened using blue visible light.

The coarse particle fraction may be selected from, but not limited to, borosilicate glass, barium magnesium aluminosilicate glass, barium aluminosilicate glass, amorphous silica, zirconium silicate, titanium silicate, barium oxide, quartz, alumina and other inorganic oxide particles. A chemical sol gel process may be used to manufacture the filler, or in an exemplary embodiment, a filler may be ground to the size range by a comminution step. The coarse filler particles may be surface treated with gamma-methacryloxypropyl trimethoxysilane or, more preferably with a long-chain polymerizable silane having the general formula:

wherein $R^1$ is a (meth)acrylate group functionalized radical; n is an integer; Z is selected from $-C(=O)-$, $-C(=S)-$, $-C(=O)-O-$, $-C(=O)-S-$, $-C(=S)-O-$, $-C(\alpha S)-S-$, $-C(=O)-NR^5-$, $-C(=S)-NR^5-$, and $-C(R^6)_2-$; Q is optional and represents an alkylene spacer, wherein the succession of carbon atoms may be interrupted by heteroatoms including N, O, or S; $R^2$ is selected from halogen or alkoxy groups; $R^3$, $R^4$ independently are selected from hydrogen, halogen, alkyl, aryl, alkoxy, and aryloxy; $R^5$ and $R^6$ independently are hydrogen, alkyl or aryl radicals.

The coarse particle fraction may also be selected from a prepolymerized filler. For example, U.S. Pat. No. 6,890,968, which is incorporated herein by reference, discloses the preparation and use of prepolymerized filler particles suitable for the present invention. The prepolymerized filler particles are prepared by mixing an inorganic filler with an organic polymerizable resin and curing the mixture. The cured mixture is then ground to a desired size. The ground prepolymerized filler may be further classified to separate the desired coarse particle fraction out of the polydisperse ground prepolymerized filler to provide the prepolymerized filler with an essentially monomodal particle size distribution. For example, the coarse particle fraction may have a mean particle size of about 30-70 μm with a D(15) of 10 μm, as disclosed in the '968 patent. Optionally, the classified ground prepolymerized filler may be surface treated with gamma-methacryloxypropyl trimethoxysilane or other suitable silanes.

The fine particle fraction may be selected from, but not limited to, borosilicate glass, barium magnesium aluminosilicate glass, barium aluminosilicate glass, amorphous silica, zirconium silicate, titanium silicate, barium oxide, quartz, alumina and other inorganic oxide particles and may be of the same or different material as the coarse particle fraction. A chemical sol gel process may be used to manufacture the filler, or in an exemplary embodiment, a filler may be ground to the desired size range by an extensive comminution step. The fine filler particles may be surface treated with gamma-methacryloxypropyl trimethoxysilane. An example for a fine particle filler particularly suitable for the present invention is disclosed in U.S. Pat. No. 6,121,344, which is incorporated herein by reference. For example, the fine particle fraction may have a mean particle size of 0.62 μm and a D(90) of 0.82 μm as prepared by Method A disclosed therein, or a mean particle size of 0.47 μm and a D(90) of 0.76 μm as prepared by Method B disclosed therein, or a mean particle size of 0.36 µm and a D(90) of 0.61 µm as prepared by Method C disclosed therein.

To further increase the loading and to increase material strength, the inventive material also comprises a nanofiller having a mean particle size of less than 100 nm. Generally, the particle size distribution for a nanofiller is less than 100 nm, with the largest particles being smaller than the smallest particles of the fine particle fraction of the structural filler. In an exemplary embodiment, the nanofiller is added at a ratio of structural filler to nanofiller of about 20 to 1 to about 10 to 1 by volume. Structural filler refers to the combined coarse and fine particle fractions. In an exemplary embodiment, the nanofiller comprises essentially discrete, non-agglomerated particles. Colloidal silica is exemplary. Fumed silica is excluded herein from the scope of nanofillers.

The rheology-modifying additive may comprise an inorganic rheology modifier, an organic rheology modifier, or particularly advantageously a combination of both. One particularly suitable inorganic rheology modifier is pyrogenic (fumed) silica. Thus, fumed silica, for purposes of this invention, falls within the category of a rheology-modifying additive, and is not considered a nanofiller. Exemplary organic rheology modifiers are small molecules or polymers capable of forming strong non-covalent intermolecular interactions such as ionic or hydrogen bonding. Specific examples of organic modifiers include those disclosed in U.S. Pat. No. 6,395,803, which is incorporated herein by reference. Alkylamide compounds, in particular, as disclosed therein are useful in the present invention. In general, as set forth in the '803 patent, alkylamides of the general formula RCONHR', where R is an alkyl or alkylidine group and R' is an alkyl group, are useful as rheology-modifying additives in dental restorative compositions, particularly where an R or R' alkyl group has 4 or more carbons and preferably 10 or more. For example, the rheology-modifying additive may be one or more of the following: (1) a hydroxyfunctional polycarboxylic acid amide; (2) the reaction product of from about 15 to 75 parts by weight of one or more liquid polyalkoxylated nitrogen-containing compounds containing more than one hydroxyl group and which also contain a pendant aliphatic radical of 6 to 40 carbon atoms selected from the group consisting of tertiary amines and amides of secondary amines, from about 8 to 90 parts by weight of one or more polycarboxylic acids, and from about 0.5 to 20 parts by weight of one or more liquid diamines of a molecular weight (weight average) of about 2000 or less, wherein the reaction is continued until the acid value is within the range of 5 to 14 and the amine value is within the range of 42 to 84; (3) trialkylamidocyclohexanes, such as trialkyl cis-1,3,5-cyclohexanetricarboxamides; (4) carbobenzyloxy-containing alkylamides, such as N-carbobenzyloxy-L-isoleucylaminooctadecane; (5) L-valine-containing benzenedicarbonyl derivatives, such as N, N' terephthaloyl-bis (L-valylaminododecane) and N, N' terephthaloyl-bis (L-valylaminooctadecane); and derivatives of trans-1,2-diaminocyclohexane, such as trans-1,2-bis(dodecylamido)cyclohexane, the polymerizable derivative (1R,2R)-trans-1,2-bis(2-(methacryloyloxy)ethylsuccinamido)cyclohexane and trans-1,2-bis(ureido)cyclohexane. It is believed that a rheology modifier of the type in example (1) above may be obtained from BYK Chemie USA, Wallingford, Conn. under the trade name BYK®-405, and that a rheology modifier of the type in example 2 above may be obtained from Rheox Corporation, Hightstown, N.J. under the trade name Thixatrol® VF-10.

In one embodiment, the rheology modifying additives may be present in an amount of about 0.1 to about 5 percent by weight of the total paste mixture. By way of example, and not limitation, the rheology-modifying additive may include a hydroxyfunctional polycarboxylic acid amide according to the Formula (1) provided in the '803 patent, which may be present in an amount of about 0.1-0.7 percent by weight. Fumed silica may be added in addition to the organic rheology modifier, for example in an amount of about 1-3 wt. %. More than one fumed silica may be used, for example each with a different average particle size, for example, a 20 nm fumed silica and a 40 nm fumed silica, and/or a combination of hydrophilic and hydrophobic fumed silicas.

The dental restorative compositions of the invention may further include a dispersant, for example, as described in the '803 patent. More specifically, phosphoric acid esters (including mono-, di- and tri-esters), such as polymerizable phosphate polyesters, may be used. Particularly, phosphoric acid esters useful in the present invention are selected from the following: a) a phosphoric acid ester containing a carboxylic acid ester group and an ether group, and b) a phosphoric acid ester containing a carboxylic acid ester group and not containing an ether group. One example of a dispersant for use in the present invention may be obtained from BYK Chemie USA, Wallingford, Conn. under the trade name Disperbyk®-111. Other examples include polycaprolactone-modified methacrylate monophosphates, such as polycaprolactone-modified hydroxyethyl methacrylate phosphate, polycaprolactone-modified hydroxyethyl acrylate phosphate, polycaprolactone-modified polypropylene glycomethacrylate phosphate, polycaprolactone-modified glycerol dimethacrylate phosphate, polycaprolactone-modified dipentaerythritol pentaacrylate phosphate, and polycaprolactone-modified polyethylene glycol monomethacrylate phosphate. By way of example, a dispersant may be present in an amount of 5 weight percent or less, such as 0.5-3.5 weight percent.

EXAMPLES

Compressive Strength (CS) Test

The specimens were prepared by condensing the dental restorative composition, in paste form (referred to simply as "the paste"), into a stainless-steel mold with a dimension of 4 mm (diameter)×3 mm (height), and then photo-curing the paste with a Demetron Optilux™ 501 curing light (Kerr Corp.) for 30-seconds from each side. The cured disk was removed from the mold and conditioned in 37° C. water for 24 hours before subjecting to mechanical testing on an Instron Universal Tester (Model 4202) in compression mode with a crosshead speed of 0.50 mm/minute. The peak load at which the specimen broke was used to calculate the CS expressed in MPa unit. Six specimens were tested for each formula.

Diametral Tensile Strength (DTS) Test

The specimens were prepared by condensing the paste into a stainless-steel mold with a dimension of 6 mm (diameter)×3 mm (height), and then photo-curing the paste with a Demetron Optilux™ 501 curing light (Kerr Corp.) for 30-seconds from each side. The cured disk was removed from the mold and conditioned in 37° C. water for 24 hours before subjecting to mechanical testing on an Instron Universal Tester (Model 4202) in compression mode with a crosshead speed of 10 mm/minute. The load was applied in the diameter direction in compression mode. The peak load at which the specimen broke was used to calculate the DTS expressed in MPa unit. Six specimens were tested for each formula.

Flexural Strength (FS) and Young's Modulus (E) Tests

FS and E were measured from the same flexural test according to ISO 4049 standard. The specimens were prepared by condensing the paste into a stainless-steel mold with a dimension of 2 mm×2 mm×25 mm, and then photo-cured from both sides. The cured disk was removed from the mold and conditioned in 37° C. water for 24 hours before subjecting to mechanical testing on an Instron Universal Tester (Model 4202) in 3-point bending mode with a crosshead speed of 0.5 mm/minute. The peak load at which the specimen broke was used to calculate the FS expressed in MPa unit. E was obtained from the slope of the stress-strain curve in the initial linear region. Five specimens were tested for each formula.

Volumetric Polymerization Shrinkage (VPS)

VPS was calculated based on the measured densities of the material before and after light-curing with the Demetron Optilux™ 501 curing light for 60 seconds (30 seconds each side). The density was measured using the buoyancy method in de-ionized water.

Complex Viscosity (eta*) and Loss Tangent (tan δ)

Rheological properties were determined using a stress-controlled dynamic oscillatory Rheometer (DSR-200, Rheometrics Scientific, Piscataway, N.J.) in parallel plate configuration with plate diameter of 10 mm and a gap of 1.0 mm at a constant frequency of 1.0 Hz. A low stress of 50 Pa was applied for 300 s and complex viscosity (eta*) in Pa·s and loss tangent were recorded. These values are indicative of the viscosity in the undisturbed state. The samples were subsequently subjected to high stress of 1000 Pa for 30 s and complex viscosity and loss tangent were recorded. These values are indicative of the viscosity when sonic or ultrasonic vibrations are applied. A Loss Tangent of less than 1 indicates solid or elastic properties that are desirable for the undisturbed state for purposes of shaping the composition to the tooth anatomy without the composition flowing under its own weight. A Loss Tangent of greater than 1 indicates liquid-like properties that are desirable for flowing the composition through a delivery means.

Abbreviations for Materials Used in all Examples:

| | |
|---|---|
| Bis-GMA | 2,2-bis[4-(2-hydroxy-3-methacryloylpropoxy)-phenyl]-propane |
| CQ | camphorquinone |
| EDMAB | ethyl 4-(N,N-dimethylamino) benzoate |
| EBPADMA-2.5EO | ethoxylated bisphenol A dimethacrylate with 2.5 moles of ethylene oxide |
| EBPADMA-6EO | ethoxylated bisphenol A dimethacrylate with 6 moles of ethylene oxide |
| MACL-TES | polymerizable polyester triethoxysilane |
| HEMA-CL5-P | polymerizable phosphate polyester:polycaprolactone-modified hydroxyethylmethacrylate with 5:1 mole ratio of caprolactone:starting material |
| MEHQ | 4-methoxyphenol |
| R-202 | fumed silica, Aerosil R-202; 14 nm primary particles; aggregated |
| ST-OX-50 | fumed silica, OX-50 surface treated with γ-methacryloyloxypropyl trimethoxysilane; 40 nm primary particles; aggregated |
| ST-BAS-0.5 | Bariumaluminoborosilicate filler, mean particle size of 0.5 µm, D(90) of 0.8 µm, surface treated with γ-methacryloyloxypropyl trimethoxysilane |
| ST-BAS-0.7 | Bariumaluminoborosilicate filler, mean particle size of 0.7 µm, D(90) of 1.1 µm, surface treated with γ-methacryloyloxypropyl trimethoxysilane |
| ST-BAS-4G | Bariumaluminoborosilicate filler, mean particle size of 4 µm, D(10) of 1.5 µm, surface treated with γ-methacryloyloxypropyl trimethoxysilane |
| ST-BAS-4P | Bariumaluminoborosilicate filler, mean particle size of 4 µm, D(10) of 1.5 µm, surface treated with MACL-TES |
| UV-9 | 2-hydroxy-4-methoxybenzophenone |
| TEGDMA | Triethyleneglycoldimethacrylate |
| BYK-405 | hydroxyfunctional polycarboxylic acid amide |

In all the examples for making the single-part, light-curable restorative material compositions, a homogeneous resin mixture was made first by mixing all monomers with initiators and additives that are soluble in the resin mixture. The resin composition is provided in Table 1. Then the resin mixture was further blended together with various fillers to make the restorative composition, in paste form. Unless otherwise indicated, all parts and percentages are by weight in all examples.

TABLE 1

| Resin Composition | |
|---|---|
| BisGMA | 9.9 weight % |
| TEGDMA | 4.9 weight % |
| EBPADMA-2.5EO | 24.7 weight % |
| EBPADMA-6EO | 59.2 weight % |
| UV-9 | 0.49 weight % |
| MEHQ | 0.06 weight % |
| CQ | 0.23 weight % |
| EDMAB | 0.49 weight % |
| Total | 100 |

The compositions used for all examples and their testing results are listed in Table 2.

TABLE 2

| Dental Restorative Compositions | | | | | | |
|---|---|---|---|---|---|---|
| | A wt % | B wt % | C wt % | D wt % | E wt % | F wt % |
| Resin | 17.8 | 17.8 | 14.9 | 19.8 | 19.3 | 15.2 |
| HEMA-CL5-P | 1.0 | 1.0 | 1.0 | 1.0 | 1.0 | 1.0 |
| Colloidal silica (80 nm, mostly non-agglomerated) | 4.0 | 4.0 | 4.0 | 4.0 | | 4.0 |
| BYK-405 | 0.2 | 0.2 | 0.2 | 0.2 | 0.2 | |
| Fumed silica | 0.5 | 0.5 | 1.2 | 0.5 | 0.5 | |
| ST-BAS-0.5 | | | 15.1 | | | |
| ST-BAS-0.7 | | 13.5 | | 60.5 | 15.0 | 15.8 |
| ST-BAS-4G | 76.5 | 63.0 | | 14.0 | 64.0 | 64.0 |
| ST-BAS-4P | | | 63.6 | | | |
| Total loading (wt %) | 81.0 | 81.0 | 83.9 | 79.0 | 79.5 | 83.8 |
| TESTING RESULTS | | | | | | |
| CS (MPa) | 258 | 277 | 363 | 360 | 256 | 299 |
| FS (MPa) | 105 | 129 | 159 | 139 | 117 | 132 |
| E (GPa) | 13.7 | 12.6 | 12.9 | 11.6 | 12.4 | 15.0 |
| DTS (MPa) | | | 55 | | | |
| VPS (%) | | 2.1 | 1.7 | | 2.2 | 1.9 |
| eta* (50 Pa stress) (Pa · s) | 20712 | 3053 | 3804 | 13460 | 1574 | 74 |
| tanδ (50 Pa stress) | 0.57 | 0.43 | 0.35 | 0.34 | 0.61 | 2.42 |
| eta* (1000 Pa stress) (Pa · s) | 1262 | 618 | 615 | 3737 | 444 | 364 |
| tanδ (1000 Pa stress) | 1.03 | 1.34 | 1.09 | 0.49 | 1.45 | 1.50 |

Example A illustrates a composition having a large particle fraction and nanofiller, but lacking a small particle fraction. While the composition undergoes shear thinning, as indicated by the reversal in the Loss Tangent, the Complex Viscosity is so high in the undisturbed state that it cannot be easily manipulated and may be considered too hard to be practically useful, and is so high in the disturbed state that it may not or will not easily flow through a desired delivery means.

Example B illustrates a composition nearly identical to that of Example A, but with a minor portion of the large particle fraction substituted by a small particle fraction in accordance with the invention. The Loss Tangent values indicate shear thinning upon vibration and the Complex Viscosities indicate good shaping and flow properties for the two states.

Example C illustrates a composition similar to Example B, but with slightly higher total filler loading, which is desirable, and an increased content of the inorganic rheology modifier to enable the higher loading. Even with the higher loading, the Loss Tangent values indicate shear thinning upon vibration and the Complex Viscosities indicate good shaping and flow properties for the two states. Additionally, low volumetric shrinkage is obtained.

Example D illustrates a composition similar to Example B, but with the quantity of small and large particle fractions essentially reversed, i.e., higher quantity of small particle fraction and lower quantity of large particle fraction. The composition exhibited little to no shear thinning, i.e., it did not transition to a liquid-like state upon application of vibration.

Example E illustrates a composition similar to Example B, but lacking the nanofiller, i.e., the non-agglomerated colloidal silica. The composition still undergoes shear thinning upon the application of vibration, but the Complex Viscosities indicate that the material is too soft in the undisturbed state such that it will begin to flow under its own weight and will be difficult to shape.

Example F illustrates a highly loaded composition similar to Example C, but lacking both the organic and inorganic rheology modifiers. The material was unacceptably soft in the undisturbed state such that it flows under its own weight, and actually experiences shear thickening upon the application of vibration.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details and method and illustrative examples shown and described. Accordingly, departures may be made from such details without departing from the scope of the general inventive concept.

What is claimed is:

1. A dental restorative composition, comprising:
   a polymerizable resin;
   a substantially translucent structural filler having a refractive index substantially similar to that of the polymerizable resin, wherein the structural filler comprises:
   a coarse particle fraction having a first mean particle size greater than 3 μm and a D(10)≥1 μm, and
   an inorganic fine particle fraction having a second mean particle size greater than 0.1 μm and less than 1 μm and a D(90) less than or equal to the D(10) of the coarse particle fraction,
   wherein a relative ratio of the coarse particle fraction to the fine particle fraction is in the range from about 12:1 to about 2:1 by volume, and the particle size distributions of each of the coarse and fine particle fractions are essentially monomodal;
   a nanofiller having a mean particle size less than 100 nm; and
   at least one rheology-modifying additive,
   wherein the composition has a viscosity that is paste-like in an undisturbed state, and the composition undergoes shear-thinning to reduce the viscosity to liquid-like in a disturbed state in which the composition is subjected to sonic and/or ultrasonic vibration.

2. The composition of claim 1, wherein the at least one rheology-modifying additive comprises an inorganic rheology modifier and an organic rheology modifier.

3. The composition of claim 2, wherein the inorganic rheology modifier is fumed silica.

4. The composition of claim 3, wherein the organic rheology modifier is an alkylamide of the general formula RCONHR', where R is an alkyl or alkylidine group and R' is an alkyl group.

5. The composition of claim 2 wherein the organic rheology modifier is an alkylamide of the general formula RCONHR', where R is an alkyl or alkylidine group and R' is an alkyl group.

6. The composition of claim 1, further comprising a polymerizable phosphate polyester dispersant.

7. The composition of claim 1, wherein the at least one rheology-modifying additive is present in an amount of about 0.1 to about 5 wt. %.

8. The composition of claim 1, wherein the nanofiller is essentially non-agglomerated colloidal silica.

9. The composition of claim 1, wherein the D(90) is ≤0.9 µm.

10. The composition of claim 1, wherein the refractive index of the structural filler minus the refractive index of the polymerizable resin is less than or equal to about 0.05.

11. The composition of claim 1, wherein the ratio of the structural filler to the nanofiller is in the range of about 20:1 to about 10:1 by volume.

12. The composition of claim 1, wherein the Loss Tangent is <1 in the undisturbed state and >1 in the disturbed state.

13. The composition of claim 1, wherein, upon curing, the composition exhibits less than about 1.8% volumetric shrinkage.

14. A dental restorative composition, comprising:
a polymerizable resin;
a substantially translucent structural filler having a refractive index substantially similar to that of the polymerizable resin, wherein the structural filler comprises:
   a coarse particle fraction having an essentially monomodal distribution with a first mean particle size greater than about 3 µm and a D(10)≥1 µm, and
   a fine particle fraction having an essentially monomodal distribution with a second mean particle size greater than 0.1 µm and less than about 1 µm and a D(90)≤0.9 µm,
wherein a relative ratio of the coarse particle fraction to the fine particle fraction is in the range from about 12:1 to about 2:1 by volume;
a nanofiller having a mean particle size less than 100 nm, wherein the ratio of the structural filler to the nanofiller is in the range of about 20:1 to about 10:1 by volume;
first and second rheology-modifying additives in an amount of about 0.1 to about 5 wt. %, wherein the first rheology-modifying additive comprises an inorganic rheology modifier and the second rheology-modifying additive comprises an organic rheology modifier, and
wherein the composition has a viscosity that is paste-like and has a Loss Tangent that is <1 in an undisturbed state, and wherein the composition undergoes shear-thinning to reduce the viscosity to liquid-like and has a Loss Tangent that is >1 in a disturbed state in which the composition is subjected to sonic and/or ultrasonic vibration.

15. The composition of claim 14, wherein the first and second rheology-modifying additives are respectively fumed silica and an alkylamide.

16. The composition of claim 14, wherein, upon curing, the composition exhibits less than about 1.8% volumetric shrinkage.

17. A dental restorative composition, comprising:
a polymerizable resin;
a substantially translucent structural filler having a refractive index substantially similar to that of the polymerizable resin, wherein the structural filler consists of:
   a coarse particle fraction having a first mean particle size greater than 3 µm, and
   a fine particle fraction having a second mean particle size greater than 0.1 µm and smaller than the first mean particle size of the coarse particle fraction, wherein a D(90) of the fine particle fraction is less than a D(10) of the course particle fraction,
   wherein a relative ratio of the coarse particle fraction to the fine particle fraction is in the range from about 12:1 to about 2:1 by volume, and the particle size distributions of each of the coarse and fine particle fractions are essentially monomodal;
a nanofiller having a mean particle size less than 100 nm;
at least one inorganic rheology-modifying additive; and
at least one organic rheology-modifying additive,
wherein the composition has a Loss Tangent<1 in an undisturbed state and a Loss Tangent>1 in a disturbed state in which sonic or ultrasonic vibration is applied.

18. The composition of claim 17, wherein the at least one inorganic rheology-modifying additive is fumed silica and wherein at least one organic rheology-modifying additive is an alkylamide of the general formula RCONHR', where R is an alkyl or alkylidine group and R' is an alkyl group.

19. The composition of claim 17, further comprising a polymerizable phosphate polyester dispersant.

* * * * *

UNITED STATES PATENT AND TRADEMARK OFFICE
CERTIFICATE OF CORRECTION

PATENT NO. : 9,237,991 B2  
APPLICATION NO. : 14/474598  
DATED : January 19, 2016  
INVENTOR(S) : Ulf Drechsler

Page 1 of 1

It is certified that error appears in the above-identified patent and that said Letters Patent is hereby corrected as shown below:

IN THE SPECIFICATION

In Col. 6, line 23, "—C($\alpha$S)—S—," should read -- —C(=S)—S—, --.

Signed and Sealed this  
Twenty-fourth Day of May, 2016

Michelle K. Lee  
*Director of the United States Patent and Trademark Office*